US00PP32640P2

(12) United States Plant Patent
Beekenkamp

(10) Patent No.: US PP32,640 P2
(45) Date of Patent: Dec. 15, 2020

(54) ***BEGONIA* PLANT NAMED 'BKPBEMCRG'**

(50) Latin Name: ***Begonia* x *hiemalis***
Varietal Denomination: BKPBEMCRG

(71) Applicant: Annie Cornelia Beekenkamp, Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 16/873,391

(22) Filed: Apr. 4, 2020

(51) Int. Cl.
*A01H 5/02* (2018.01)
*A01H 6/18* (2018.01)

(52) U.S. Cl.
USPC ..... Plt./349
CPC ..... *A01H 6/185* (2018.05)

(58) Field of Classification Search
USPC ..... Plt./349
CPC ..... A01H 6/185; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Begonia* plant named 'BKPBEMCRG', characterized by its broadly upright and mounded plant habit; sturdy plants with freely basal branching habit; dark green-colored leaves; uniform and freely flowering habit; and single flowers that are red in color.

2 Drawing Sheets

Figure 1:
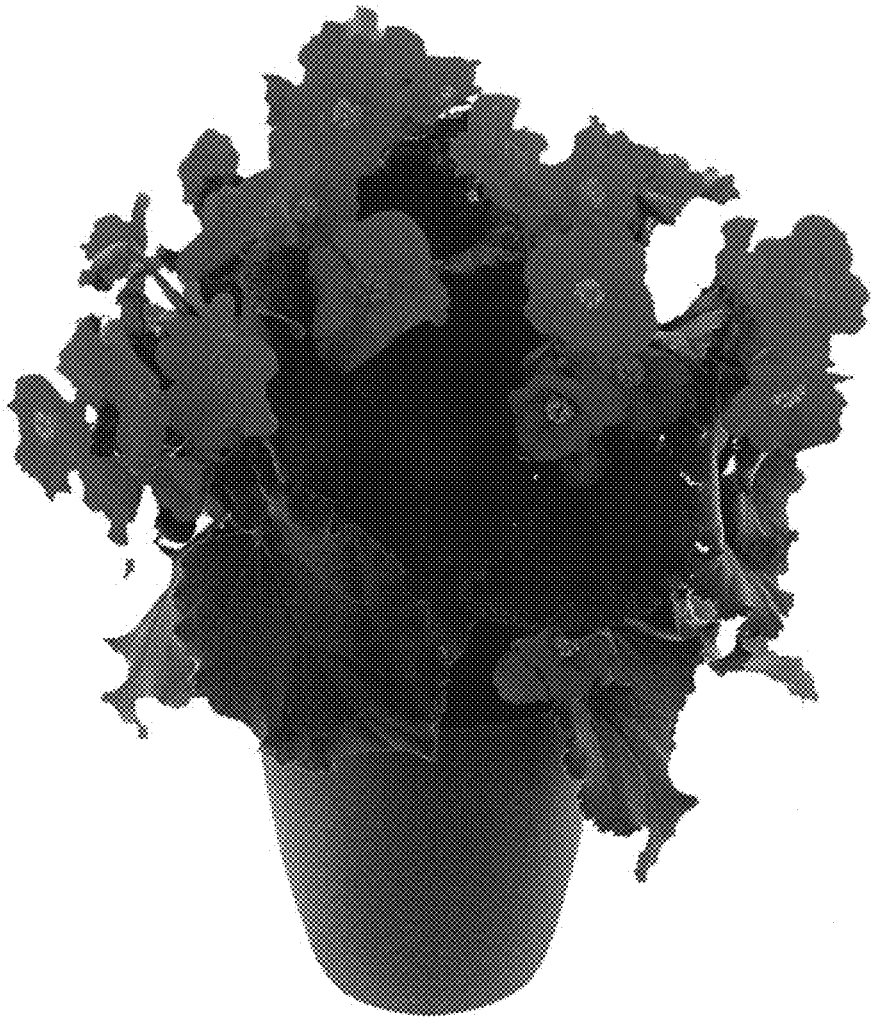

Botanical designation: *Begonia* x *hiemalis*.
Cultivar denomination: 'BKPBEMCRG'.

BACKGROUND OF THE INVENTION

The present invention relates to a new and distinct cultivar of *Begonia* plant, botanically known as *Begonia* x *hiemalis*, commercially referred to as Elatior *Begonia* and hereinafter referred to by the name 'BKPBEMCRG'.

The new *Begonia* plant is a product of a planned breeding program conducted by the Inventor in Maasdijk, The Netherlands. The objective of the breeding program was to develop new freely branching and freely flowering *Begonia* plants with attractive flowers and good garden performance.

The new *Begonia* plant originated from a cross-pollination made by the Inventor in May, 2015 of a proprietary selection of *Begonia* x *tuberhybrida* identified as code number 09-0008-03, not patented, as the female, or seed, parent with an unnamed proprietary selection of *Begonia socotrana*, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in October, 2015.

Asexual reproduction of the new *Begonia* plant by vegetative tip cuttings in a controlled greenhouse environment in Maasdijk, The Netherlands since March, 2016 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEMCRG'. These characteristics in combination distinguish 'BKPBEMCRG' as a new and distinct *Begonia* plant:

1. Broadly upright and mounded plant habit.
2. Sturdy plants with freely basal branching habit.
3. Dark green-colored leaves.
4. Uniform and freely flowering habit.
5. Single flowers that are red in color.

Plants of the new *Begonia* can be compared to plants of the female parent selection. Plants of the new *Begonia* differ primarily from plants of the female parent selection in the following characteristics:

1. Leaves of plants of the new *Begonia* are dark green in color whereas leaves of plants of the female parent selection are reddish green in color.
2. Leaves of plants of the new *Begonia* are glabrous whereas leaves of plants of the female parent selection are pubescent.

Plants of the new *Begonia* can be compared to plants of the male parent selection. Plants of the new *Begonia* differ primarily from plants of the male parent selection in the following characteristics:

1. Plants of the new *Begonia* have red-colored flowers whereas plants of the male parent selection have pink-colored flowers.
2. Flowers of plants of the new *Begonia* do not produce pollen whereas flowers of plants of the male parent selection produce pollen.

Plants of the new *Begonia* can be compared to plants of *Begonia* x *hiemalis* 'BKPBECRM', disclosed in U.S. Plant Pat. No. 28,818. Plants of the new *Begonia* differ primarily from plants of 'BKPBECRM' in the following characteristics:

1. Leaves of plants of the new *Begonia* are larger and darker green in color than leaves of plants of 'BKPBECRM'.
2. Plants of the new *Begonia* have single-type flowers whereas plants of 'BKPBECRM' have double-type flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) comprises a side perspective view of a typical flowering plant of 'BKPBEMCRG' grown in a container.

Figure 2:
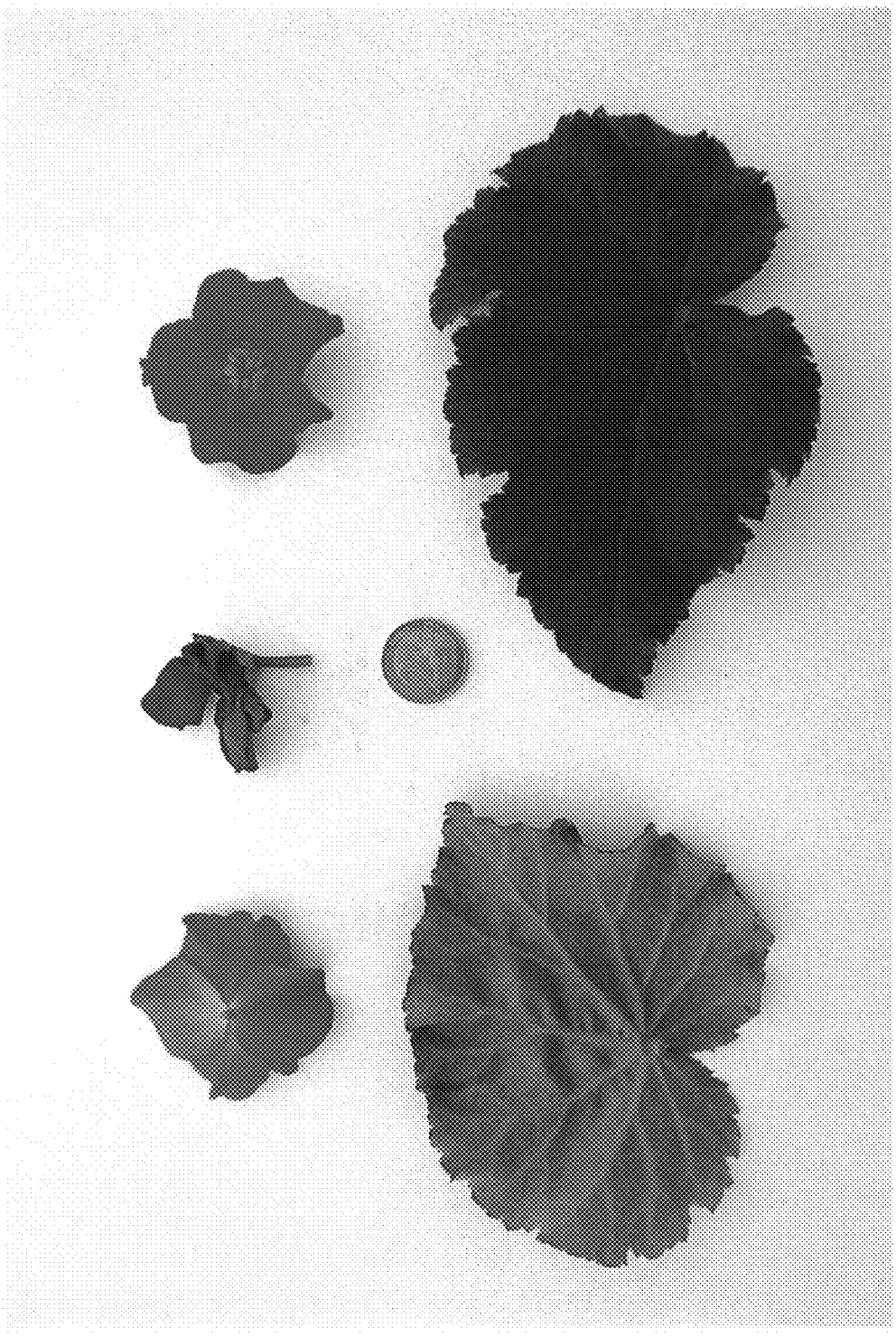

The photograph on the second sheet (FIG. 2 of 2) are close-up views of a typical flower bud and the upper and lower surfaces of typical developed flowers and leaves of 'BKPBEMCRG'.

DETAILED BOTANICAL DESCRIPTION

Plants used for the aforementioned photographs and following observations and measurements were grown during the summer in 10.5-cm containers in a glass-covered greenhouse in Dinslaken, Germany. During the production of the plants, day and night temperatures ranged from 19° to 21° C. Plants were eleven weeks from planting rooted cuttings when the photographs and the description were taken. In the following description, color references are made to The Royal Horticultural Society Colour Chart, 2015 Edition, except where general terms of ordinary dictionary significance are used.

Botanical classification: *Begonia* x *hiemalis* 'BKPBEMCRG'.

Parentage:

*Female, or seed, parent*.—Proprietary selection of *Begonia* x *tuberhybrida* identified as code number 09-0008-03, not patented.

*Male, or pollen, parent*.—Unnamed proprietary selection of *Begonia socotrana*, not patented.

Propagation:

*Type*.—By vegetative tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; typically brown in color, actual color of the roots is dependent on substrate composition, water quality, fertilizer type and formulation, substrate temperature and physiological age of roots; plants of the new *Begonia* have not been observed to form tubers.

*Rooting habit*.—Freely branching habit; dense.

Plant description:

*Plant and growth habit*.—Broadly upright and mounded plant habit; overall plant shape, globular; moderately vigorous growth habit and moderate growth rate.

*Plant height, soil level to top of foliar plane*.—About 21.6 cm.

*Plant height, soil level to top of floral plane*.—About 26.1 cm.

*Plant width*.—About 31.6 cm.

*Lateral branch description*.—Branching habit: Freely branching habit with about three basal branches each with about three lateral branches developing per plant; pinching is not required. Length: About 9.9 cm. Diameter: About 9 mm. Internode length: About 2.7 cm. Strength: Moderately strong. Aspect: About 25° from vertical. Texture and luster: Sparsely pubescent; moderately glossy. Color, developing: Close to 152B slightly tinged with close to N199A. Color, fully developed: Close to 152A.

*Leaf description*.—Arrangement: Alternate, simple. Length: About 15.4 cm. Width: About 10 cm. Shape: Ovate. Apex: Acute. Base: Oblique, lobes not imbricate to imbricate. Margin: Dentate to crenate; moderately to strongly undulate. Texture and luster, upper surface: Smooth, glabrous; velvety; slightly glossy. Texture and luster, lower surface: Smooth, glabrous, venation, sparsely pubescent; velvety; slightly glossy. Venation pattern: Pinnate. Color: Developing leaves, upper surface: Darker than 147A. Developing leaves, lower surface: Close to 197B. Fully expanded leaves, upper surface: Darker than 147A; venation, close to 147B and proximally, close to 187C. Fully expanded leaves, lower surface: Close to 148B slightly to moderately tinged with close to 182C; venation, close to 199A to 199B. Petioles: Length: About 7 cm. Diameter: About 5.5 mm. Strength: Moderately strong, flexible. Texture and luster, upper and lower surfaces: Moderately pubescent; moderately glossy. Color, upper surface: Slightly darker than 152A; distally, close to 187C. Color, lower surface: Close to 152A; distally, close to 187C. Stipules: Quantity per leaf: Two. Length: About 1 cm. Width: About 9 mm. Shape: Broadly ovate. Apex: Obtuse. Base: Broadly cuneate. Margins: Entire, ciliate. Color, upper and lower surfaces: Close to 146D; towards the margins, close to 179C.

Flower description:

*Flowering habit*.—Rotate single-type male flowers arranged in axillary compound cymes; freely flowering habit with about nine flowers per cyme and about 150 flowers developing per plant during the flowering season; flowers face upright to outwardly.

*Fragrance*.—None detected.

*Natural flowering season*.—Long flowering period, plants flower freely and continuously from spring into the autumn in The Netherlands; during the winter in a greenhouse, plants begin flowering about five weeks after exposure to photoinductive treatments.

*Postproduction longevity*.—Individual flowers last about ten days on the plant; flowers not persistent; plants maintain good substance for about 20 to 30 days in an interior environment.

*Inflorescence height*.—About 14.2 cm.

*Inflorescence diameter*.—About 11.4 cm.

*Flower buds*.—Length: About 2.1 cm. Diameter, flattened: About 7 mm to 23 mm. Shape: Reniform; flattened. Texture and luster: Smooth, glabrous; velvety; matte. Color: Close to 46A; towards the base, close to 45A.

*Flowers*.—Diameter: About 5.8 cm. Depth: About 1.8 cm. Tepals: Quantity and arrangement: Five, occasionally six, per flower arranged in two whorls. Length, lower tepals: About 3 cm. Width, lower tepals: About 3.3 cm. Length, upper tepals: About 2.8 cm. Width, upper tepals: About 2.5 cm. Shape, lower tepals: Roughly reniform. Shape, upper tepals: Broadly obovate. Apex, lower tepals: Rounded. Apex, upper tepals: Obtuse. Base, lower tepals: Broadly cuneate. Base, upper tepals: Cuneate. Margin, lower and upper tepals: Entire; moderately undulate. Texture and luster, lower and upper tepals, upper surface: Smooth, glabrous, velvety; matte. Texture and luster, lower and upper tepals, lower surface: Smooth, glabrous, velvety; matte and at the base, slightly glossy. Color, lower tepals: When opening, upper surface: Close to between 44A and 44B. When opening, lower surface: Close to 42B; towards the apex and margins, close to 42A. Fully opened, upper surface: Close to 44B; venation, close to 44B; color does not fade with development. Fully opened, lower surface: Close to 42A; venation, close to 42A; color does not fade with development. Color, upper tepals: When opening, upper surface: Close to between 44A and 44B. When opening, lower surface: Close to 44C; towards the apex and margins, close to 42A. Fully opened, upper surface: Close to 44B; venation, close to 44B; color does not fade with development. Fully opened, lower surface: Close to between 44B and 44C; venation, close to between 44B and 44C; color does not fade with development. Tepaloids: Quantity and arrangement: If present, up to seven arranged in a single whorl at the center of the flower. Length: About 1.8 cm. Width: About 1.1 cm. Shape: Obovate. Apex: Obtuse. Base: Cuneate. Margin: Entire; slightly to moderately undulate. Texture and luster, upper and lower surfaces: Smooth, glabrous, velvety; matte. Color: When opening, upper surface: Close to between 44A and 44B. When opening, lower surface: Close to 44C. Fully opened, upper surface: Close to 44B; venation, close to 44B; color does not change with development. Fully opened, lower surface: Close to between 44B and 44C; venation, close to between 44B and 44C; color does not change with development.

*Peduncles*.—Length: About 7.1 cm. Diameter: About 5 mm. Angle: About 35° from lateral branch axis. Strength: Moderately strong; flexible. Texture and luster: Sparsely pubescent; moderately glossy. Color: Close to 152B.

*Pedicels*.—Length: About 3 cm. Diameter: About 2 mm. Angle: About 45° from the peduncle axis. Strength: Moderately strong; flexible. Texture and luster: Moderately pubescent; glossy. Color: Close to 179A.

*Flower bracts*.—Quantity and arrangement: Two per flower, opposite. Length: About 1.6 cm. Width: About 1.5 cm. Shape: Broadly ovate to roughly rhomboidal. Apex: Acute. Base: Broadly cuneate. Margin: Finely serrate; ciliate. Texture and luster, upper and lower surfaces: Smooth, glabrous; slightly glossy. Color, upper and lower surfaces: Close to between 178B and 178C; proximally, close to 178B.

*Reproductive organs*.—Androecium: Stamen quantity per flower: About 25. Filament length: About 4 mm. Filament color: Close to 14A becoming closer to 24A with development. Anther size: About 1.5 mm by 2 mm. Anther shape: Obovate. Anther color: Close to 14A becoming closer to 24A with development. Amount of pollen: None observed.

*Seeds and fruits*.—Seed and fruit development have not been observed on plants of the new *Begonia* as only male flowers develop.

Pathogen & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKPBEMCRG' as illustrated and described.

* * * * *